United States Patent [19]
Thrailkill

[11] Patent Number: 5,822,053
[45] Date of Patent: Oct. 13, 1998

[54] MACHINE VISION LIGHT SOURCE WITH IMPROVED OPTICAL EFFICIENCY

[76] Inventor: William Thrailkill, 145 Ward St., Suite #45, Revere, Mass. 02151

[21] Appl. No.: 796,876

[22] Filed: Feb. 7, 1997

Related U.S. Application Data

[63] Continuation of Ser. No. 428,466, Apr. 25, 1995, abandoned.

[51] Int. Cl.⁶ ............................. G01N 21/88; F21V 3/00
[52] U.S. Cl. ..................... 356/237; 250/559.08; 362/11; 362/800; 359/385
[58] Field of Search .................................... 356/237, 394; 362/252, 11, 33, 234, 800, 246; 359/385, 388, 389; 250/559.08, 223 R, 559.39

[56] References Cited

U.S. PATENT DOCUMENTS

| | | | |
|---|---|---|---|
| 4,309,073 | 1/1982 | Nishimura et al. . | |
| 4,672,201 | 6/1987 | Welker | 356/401 |
| 4,677,473 | 6/1987 | Okamotot et al. . | |
| 4,695,720 | 9/1987 | Rieder et al. | 250/237 G |
| 4,893,223 | 1/1990 | Arnold | 356/237 |
| 4,947,078 | 8/1990 | Rice et al. | 313/113 |
| 4,972,093 | 11/1990 | Cochran et al. . | |
| 5,038,258 | 8/1991 | Koch et al. | 356/237 |
| 5,167,556 | 12/1992 | Stein | 445/24 |

OTHER PUBLICATIONS

Novini, Amir, *Fundamentals of Machine Vision Lighting*, Jun. 1985.

*Primary Examiner*—Hoa Q. Pham
*Attorney, Agent, or Firm*—Cesari and McKenna, LLP

[57] ABSTRACT

The present invention relates to an LED light source for a machine vision system. The light source includes a plurality of LEDs each arranged in a base plate in predetermined manner during manufacturing. Each LED is then securely mounted to the base plate with an ultravioletly curable adhesive to remain pointed in the predetermined manner. The light source also includes an optically efficient non-lambertain diffuser which receives light from each of the LEDs and breaks the light up to provide a uniform light field to illuminate an object under inspection.

4 Claims, 11 Drawing Sheets

MACHINE VISION LIGHT SOURCE WITH IMPROVED OPTICAL EFFICIENCY

CROSS REFERENCE TO RELATED APPLICATIONS

This application is a continuation of Ser. No. 08/428,466 filed Apr. 25, 1995, now abandoned.

TECHNICAL FIELD

The present invention relates to machine vision, and in particular to an light emitting diode light source for a machine vision system.

BACKGROUND OF THE INVENTION

Machine vision relates to automated product inspection, and is generally used for quality inspection during product manufacturing. The basic elements used in a machine vision system are similar to those employed by a human inspector: i) a sensor (i.e., the eye) to take a picture of the object under inspection and ii) a comparator (i.e., the brain) which compares the picture formed by the sensor against a known reference. So in its simplest form, a machine vision system compares a picture of what it sees against a known reference.

Figure 1:
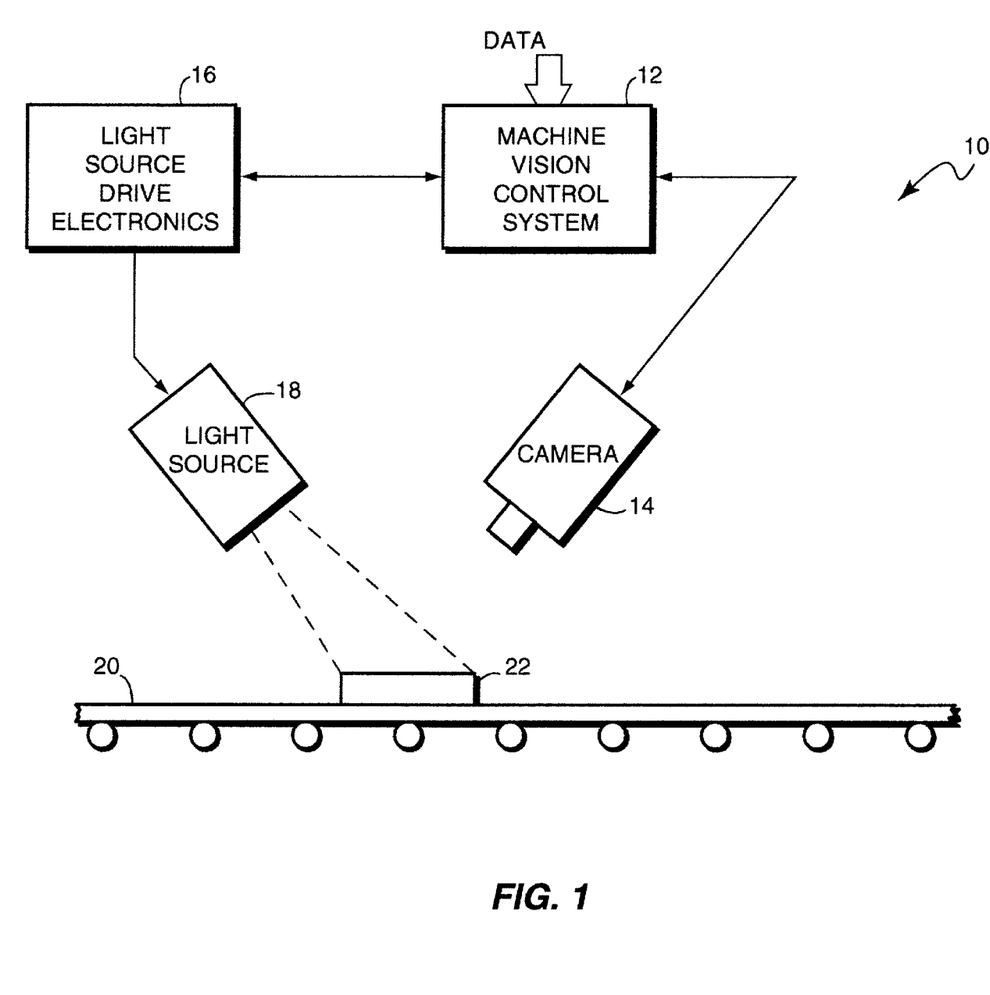
FIG. 1 illustrates a functional block diagram of a machine vision system.

FIG. 1 illustrates a functional block diagram of a machine vision system 10. The system includes a machine vision control system 12 which controls the operation of a video camera 14, and receives analog video data from the camera 14. The machine vision control system 12 also provides control signals to drive electronics 16 which drive a light source 18. As an object to be inspected 22 moves along a conveyer belt 20, the object is illuminated with light from the light source 18, and the camera 14 captures an image of the illuminated object. The camera then transmits an analog signal indicative of the image to the machine vision control system 12 which digitizes the image and compares the digitized image against a known reference. If the digitized image is outside a certain predetermined tolerance in comparison to the known reference, the object under inspection 22 fails the inspection.

Recent improvements to machine vision systems have concentrated on the sensors (e.g., solid-state cameras) and the processing techniques for comparing the digitized image of the object under inspection against the image stored in the machine vision control system. However, the quality of the image captured by the camera is also highly dependent upon the quality of the light which illuminates the object under inspection.

In general, the light source is positioned to provide the camera with the most contrast between the key features of the object under inspection and the object's background. For example, the light source may be positioned to backlight the image under inspection, to front light the image, or at an angle to the object as shown in FIG. 1.

There are several types of illumination sources which can be used to illuminate the object under inspection. Suitable choice includes incandescent bulbs, fluorescent tubes, Xenon flash tubes, lasers, light emitting diodes, and X-ray tubes. In recent years the popularity of light emitting diodes (infrared and visible) has increased due to their relatively small size, long life, low power dissipation and fast switching speed which allows them to be used in a strobed lighting source.

An example of a machine vision light source which uses light emitting diodes is disclosed in U.S. Pat. No. 4,972,093 (hereinafter the "'093 patent") entitled "Inspection Lighting System". A problem with this system is its lack of efficiency since the LEDs, although mounted to a securing means, are not arranged to point the light emitted from each LED in a predetermined manner. Therefore, in order to get a uniform light field from the light source a lambertian diffuser is used to diffuse the light from each of the LEDs.

Figure 2:
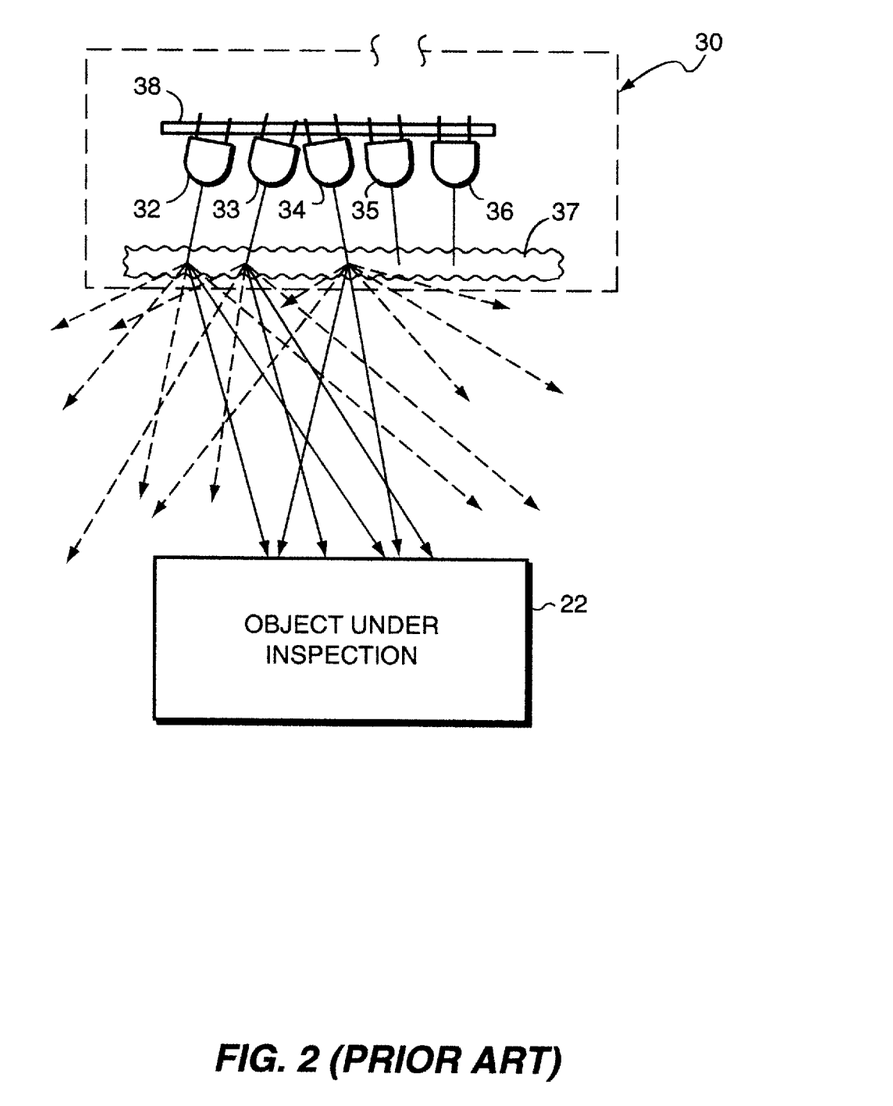
FIG. 2 illustrates a prior art LED light source which includes a plurality of LEDs and a lambertain diffuser.

To demonstrate the inefficiency of the prior art, FIG. 2 illustrates a prior art LED light source 30 which includes a plurality of LEDs 32–36 mounted to a base plate 38. Although each of the LEDs 32–36 is mounted to the base plate 38, the LED9 are not pointed at a predetermined location. Therefore, in order to generate a uniform light field to illuminate the object under inspection 22, an lambertain diffuser 37 is used. When a light ray 38 strikes the lambertain diffuser 37, the light is widely dispersed. Therefore, as shown, much of the light generated by the LEDs never illuminates the object under inspection, and hence the prior art diffusers are very inefficient.

Prior art diffusers generally include: (1) ground glass, or (2) flashed opal glass. In a ground glass diffuser the surface of the diffuser is pitted so as to scatter light, and if the pits completely cover the surface and are randomly placed, the diffuser operates as a Lambertain diffuser. Flashed opal glass diffusers include fine translucent particles fused into the surface of the glass to disperse the light to create a Lambertain diffuser.

Although the diffusers used in prior art LED light sources are effective at diffusing the light from each LED, they are also very inefficient. That is, as shown in FIG. 2, only a fraction of the total light from the LEDs actually illuminates the object under inspection 22.

Due to this inefficiency, additional LEDs have to be added to the light source 30 in order to achieve the necessary illumination of the object to be inspected. This increases the size of the light source 30, the power consumption of the light source and its drive electronics, and decreases the mean time between failure (MBTF) of the light source and the drive electronics since additional components are present.

Therefore, there is a need for a machine vision light inspection system which includes a more efficient LED light source.

SUMMARY OF THE INVENTION

An object of the present invention is to provide a machine vision LED light source with improved efficiency.

Another object of the present invention is to provide a machine vision LED light source which is smaller than prior art LED light sources.

Briefly, an LED light source includes a plurality of LEDs mounted to a base plate and each aligned in a predetermined manner. The light from each of the LEDs impinges upon a highly efficient diffuser which produces a relatively uniform light field which illuminates the object to be inspected.

The present invention is premised on the design approach of increasing efficiency of the light source (i.e., make better use of the light) rather than simply increasing the number of LEDs to increase the light output.

To align each LED in a predetermined manner, each LED is placed in the base plate and pointed such that the light exiting the LED illuminates a known location. Each LED is then securely mounted to the base plate such that it remains in its predetermined position.

The LED light source of the present invention uses a more efficient diffuser in comparison to the lambertain diffusers of the prior art. A preferred diffuser is an injection molded optically transparent component which is relatively inexpensive and breaks up the light from the LEDs rather than significantly redirecting the light.

An advantage of the present invention is that by arranging the LEDs in a predetermined manner, a more efficient optical diffuser can be used, and therefore less LEDs are required to illuminate the object under inspection in comparison of the LED light sources of the prior art.

Although the primary advantages of the present invention are improved efficiency and reduction in size, there are a number of other secondary benefits. For example, since less LEDs are used in the light source of the present invention, it is contemplated that the failure rate of the light source will be lower than prior art devices. In addition, due to the reduced size of the light source, the source can now be placed in tight confines and positioned closer to the object under inspection.

These and other objects, features and advantages of the present invention will become more apparent in light of the following detailed description of preferred embodiments thereof, as illustrated in the accompanying drawings.

DETAILED DESCRIPTION OF THE INVENTION

Figure 3:
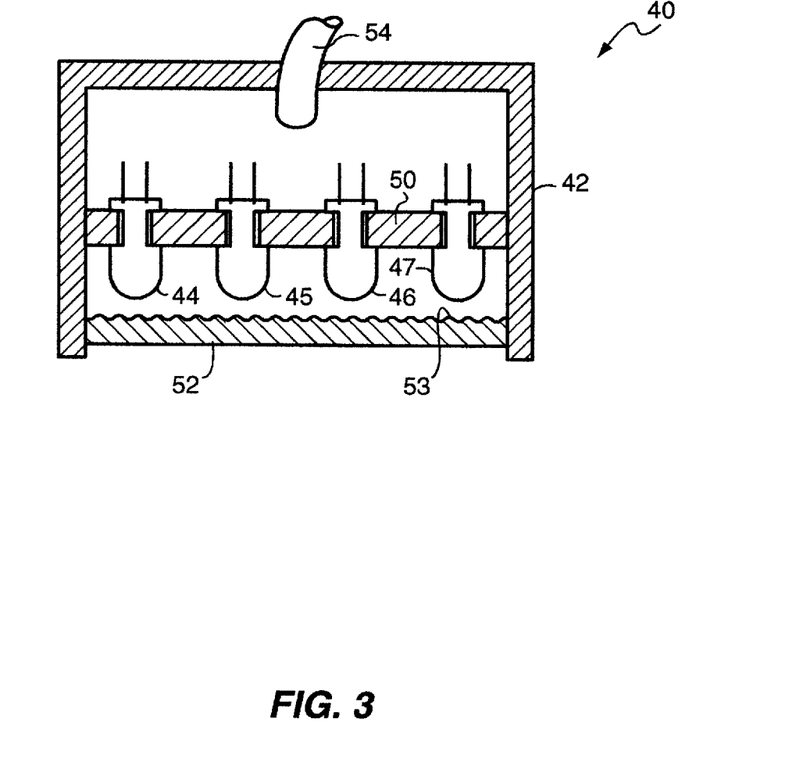
FIG. 3 illustrates a sectional view of a machine vision light source according to the present invention.

FIG. 3 illustrates a cut-away view of a machine vision light source 40 according to the present invention. The light source 40 includes a housing 42 within which a plurality of LEDs 44–47 are rigidly mounted to a base plate 50. Each LED is mounted to the base plate 50 in a predetermined manner (i.e., pointed) to control the area which is illuminated by each LED. The light source also includes an efficient diffuser 52, and a power cord 54 which carries the electrical power and control signals to the plurality of LEDs 44–47. In a preferred embodiment the LEDs are of the type which generate red visible light. The details of how the LEDs are pointed, and the characteristics of the diffuser 52 will also be discussed hereinafter.

Figure 4:
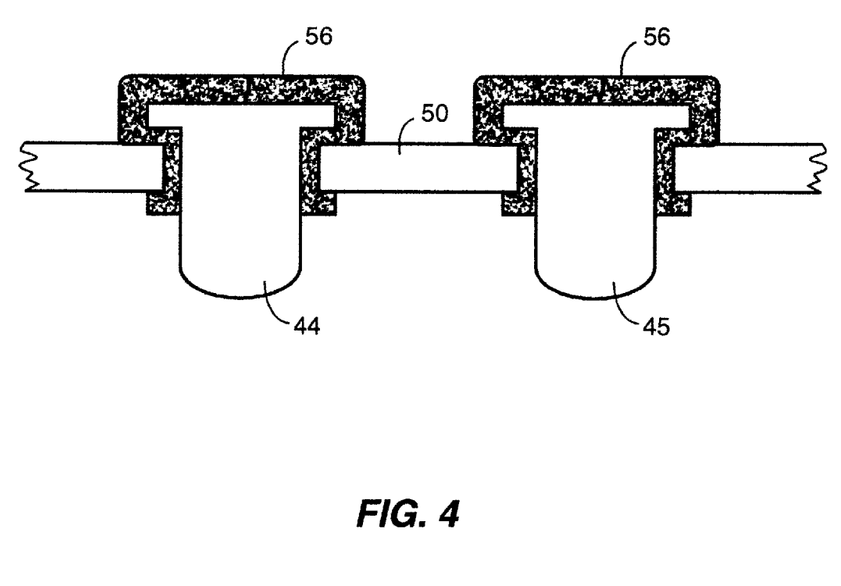
FIG. 4 illustrates several of the LEDs within the light source of FIG. 3 held in place with an ultravioletly cured adhesive.

FIG. 4 illustrates several of the LEDs 44,45 rigidly mounted to the base plate 50 by a curable adhesive 56 which locks each LED in place within an opening in the base plate. Once an LED is pointed in the predetermined manner, the adhesive 56 is applied (e.g., using a syringe) and then cured using an ultraviolet source (not shown). Once cured, the adhesive 56 rigidly surrounds the LED, locking it in place in the base plate opening. Therefore, although an adhesive is used, the adhesive primarily acts to lock the LED in place within the opening when cured, rather than bond the LED to the base plate 50. A suitable adhesive is LITE TAK 375 available from Loctite Corporation. In general, any ultravioletly curable adhesive which when cured, becomes sufficiently hard to lock the LED in place, is suitable. The details of how each of the LEDs in the light source are pointed will now be presented.

Figure 5A:
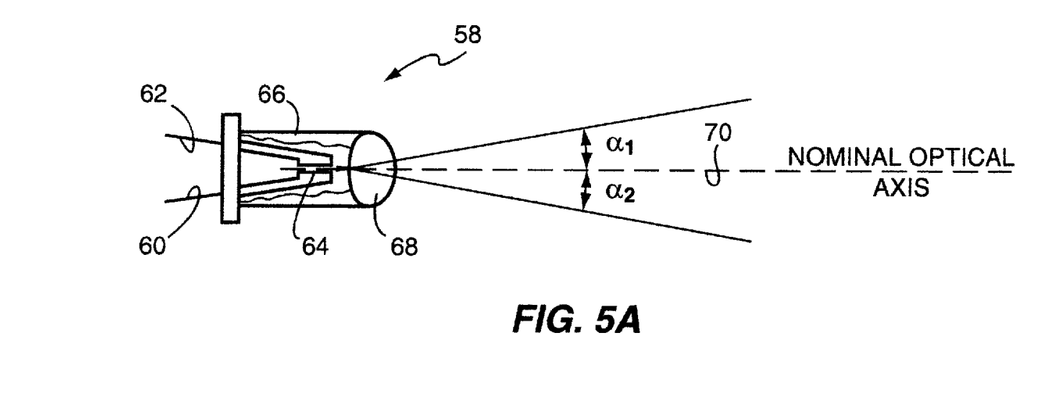
FIG. 5A illustrates an ideal LED and a light beam output therefrom, wherein the light beam is symmetrically centered about the optical axis of the LED.

FIG. 5A illustrates an ideal LED 58 which includes electrical leads 60,62, a light emitting junction 64, a body 66 (e.g., cast resin) and a focusing lens 68 located at the light output end of the LED. Light (visible or infrared) from the ideal LED 58 exits through the focusing lens 68, and is symmetric about an optical axis 70. That is, the beam of light from the ideal LED 58 is evenly spaced about the optical axis 70 such that $\alpha_1 = \alpha_2$. This relationship is only true for an ideal LED.

Figure 5B:
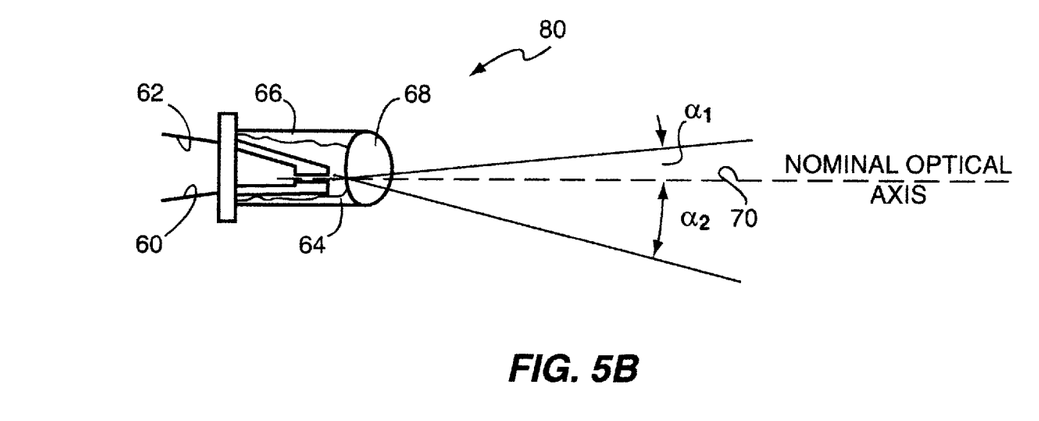
FIG. 5B illustrates a non-ideal LED wherein the light beam from the LED is not symmetrically centered about the optical axis of the LED.

FIG. 5B illustrates a non-ideal LED 80. The non-ideal LED 80 is physically the same as the ideal LED 58 and therefore the numerical designation of the elements shall remain the same. The difference between the ideal and non-ideal LEDs 58, 80, respectively, is the manufacturing tolerances which prevent the light beam from the non-ideal LED 80 from being symmetrical about the optical axis 70 (i.e., $\alpha_1 \neq \alpha_2$). Although obvious to one of ordinary skill in the art, it should be noted that the LEDs used in the machine vision light source of the present invention are non-ideal LEDs.

Figure 6A:
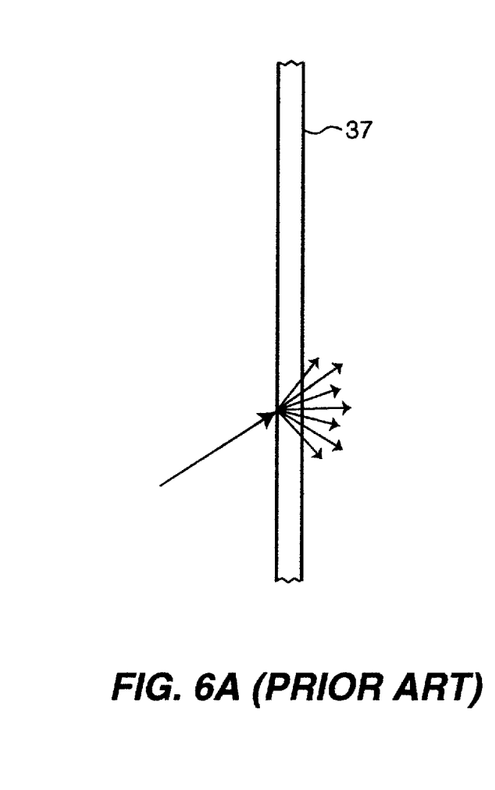
FIG. 6A illustrates a light ray striking a prior art lambertain diffuser.
Figure 6B:
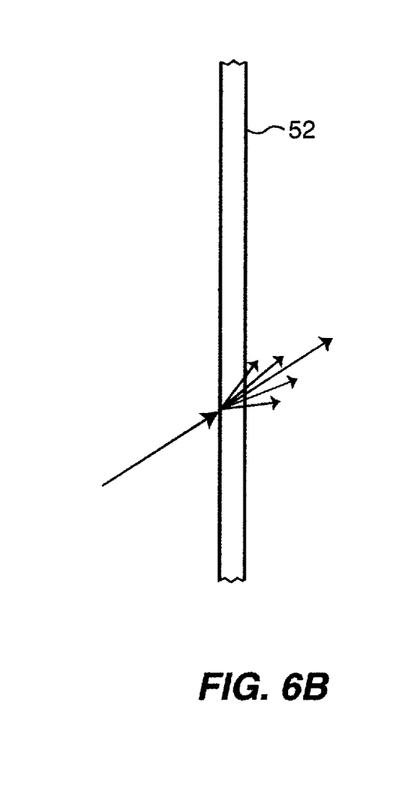
FIG. 6B illustrates a light ray striking an optically efficient diffuser.

Since the light output from a non-ideal LED 80 is generally non-symmetrical about the nominal axis 70, prior art LED light sources use a lambertain diffuser in order to provide light which uniformly illuminates the object under inspection. In contrast, to produce the light source of the present invention, during manufacturing each LED is pointed in a predetermined manner, and then securely mounted to the base plate to remain pointed in the predetermined manner. The functional difference between the efficient diffuser 52 used in the present invention, and the lambertain diffuser can be better understood following a comparison of FIGS. 6A and 6B. FIGS. 6A illustrates a light ray 81 striking a lambertain diffuser 37. The lambertain diffuser 37 is such a good diffuser, the energy of the light is dispersed in a wide area. In contrast, as shown in FIG. 6B, when a light ray 82 strikes the efficient diffuser 52 of the present invention, a small amount of the total light energy is dispersed.

Figure 7:
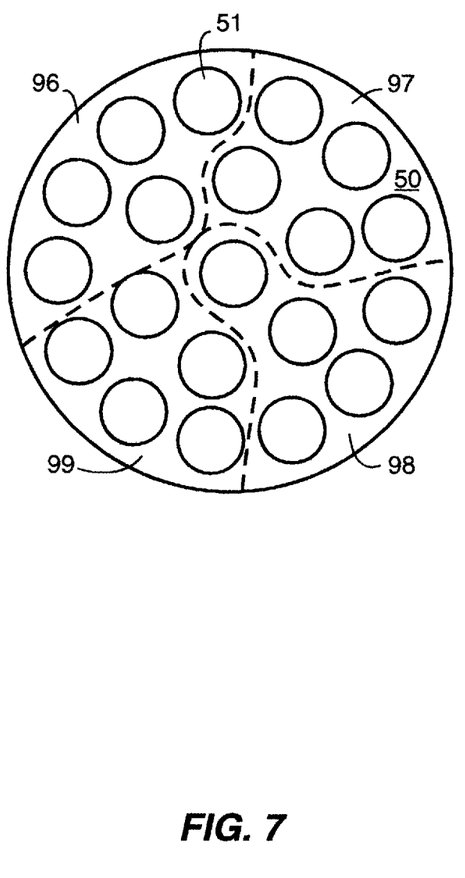
FIG. 7 illustrates a bottom view of the LEDs mounted to the base plate of the machine vision light source shown in FIG. 3.
Figure 8:
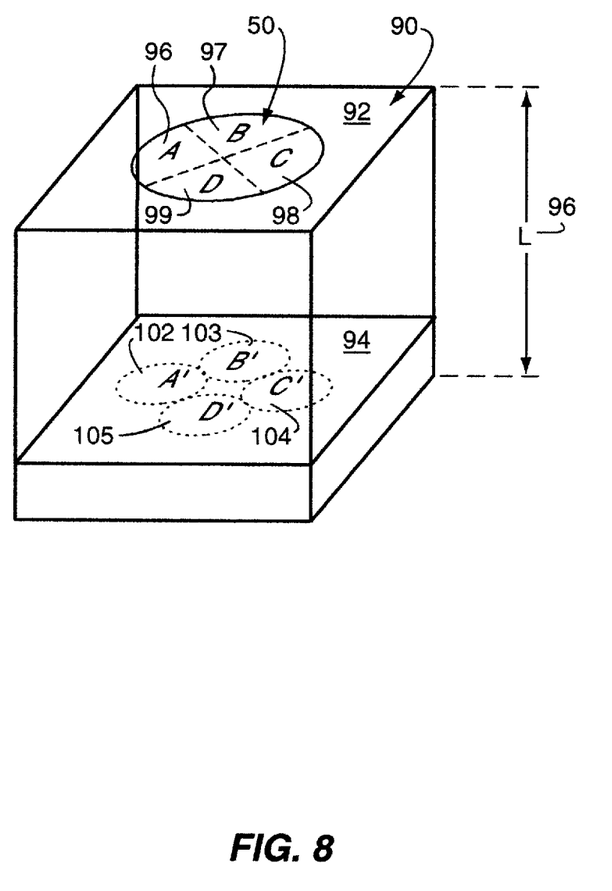
FIG. 8 illustrates a alignment fixture used to hold the base plate containing the LEDs so the LEDs can be arranged/pointed in a predetermined manner.

FIG. 7 illustrates a bottom view of the baseplate 50 and the plurality of openings (e.g., opening 51) therein. During manufacturing the base plate 50 is seated over an aperture in an alignment fixture 90 as shown in FIG. 8, and the LEDs are individually placed into their respective openings in the base plate 50 and aimed at a target that has been selected for a particular application. Referring to FIG. 8, the alignment fixture 90 includes a cover 92 containing the aperture therein which receives the base plate 50. Note, in the interest of ease of illustration, the LEDs are not shown positioned in the base plate placed in the opening on the cover 92. The LEDs (not shown) are each positioned such that the focusing lens 68 (FIG. 5B) of each LED is pointed at a bottom surface 94 of the alignment fixture, which is ideally separated from the focusing lenses 68 by a distance L 96 which is equal to the distance the light source 40 (FIG. 3) will be separated from the object it illuminates.

While mounted in the alignment fixture 90, power is individually applied to each LED, and the illuminated LED is then positioned such that the light exiting the LED illuminates a predetermined location on the bottom surface 94. For example, the LEDs in the base plate 50 can be divided into quadrants A–D 96–99, and the light from each LED will be pointed to illuminate a corresponding quadrant A'–D' 102–105 located on the bottom surface 94. Once an LED is pointed so it illuminates the area covered by its associated quadrant, the ultra-violet curable adhesive is applied to the LED (as shown in FIG. 4) to hold the LED pointed in that direction. This process is repeated for each LED.

Referring to FIGS. 7 and 8, consider for example one embodiment having twenty LEDs such that each quadrant A–D 96–99 includes five LEDs. The five LEDs in quadrant A 96 are each pointed to illuminate quadrant A' 102 while the five LEDs in quadrant B 97 are each pointed to illuminate quadrant B' 103. The LEDs in quadrants C 98 and D 99 are similarly pointed to illuminate quadrants C' 104 and D' 105, respectively. In order to get relatively even light distribution from the light source without the use of a lambertain diffuser, the location of quadrants A'–D' 102–105 on the bottom surface 94 are selected to overlap in a predetermined manner which shall now be discussed.

Figure 9:
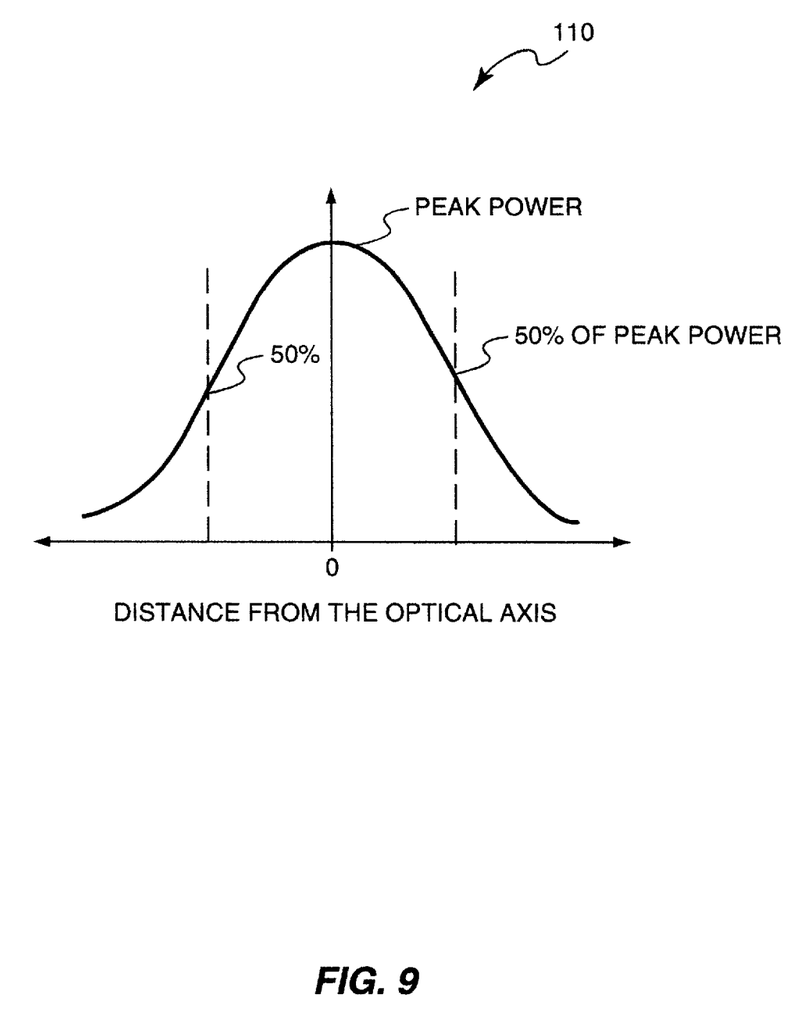
FIG. 9 is a plot of LED illumination as a function of distance from the optical axis of the LED.

FIG. 9 illustrates a plot 110 of light power as a function of the distance from the optical axis for the LED. Power is plotted along the vertical axis while the distance from the optical axis 70 (FIG. 5B) is plotted along the horizontal axis. As shown, the light distribution is generally gaussian with peak optical output occurring along the optical axis.

Figure 10:
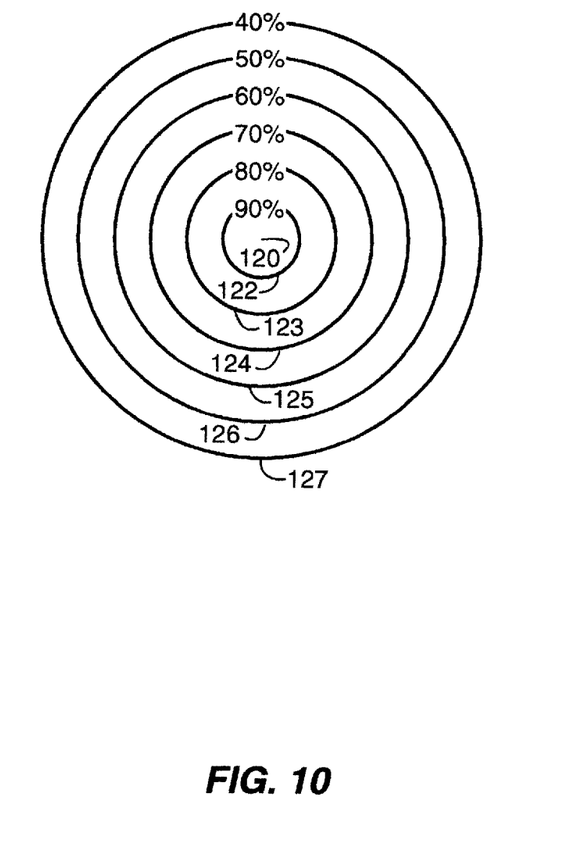
FIG. 10 is a plot of LED illumination as a function of the distance from the optical axis of the LED, wherein each concentric circle is a measure of optical power.

Referring to FIG. 10, the power distribution of light from an LED can also be represented as a group of concentric circles 122–127, where each circle is indicative of a measure of illumination. The center 120 of the concentric circles 122–127 represents the spot through which the optical axis 70 (FIG. 5B) passes, and the location of the peak optical power (i.e., 100% optical power). The first concentric circle 122 from the center 120 represents 90% peak optical power while the second concentric circle 123 represents 80% peak optical power. As the distance from the center 120 increases, the optical power decreases.

Figure 11:
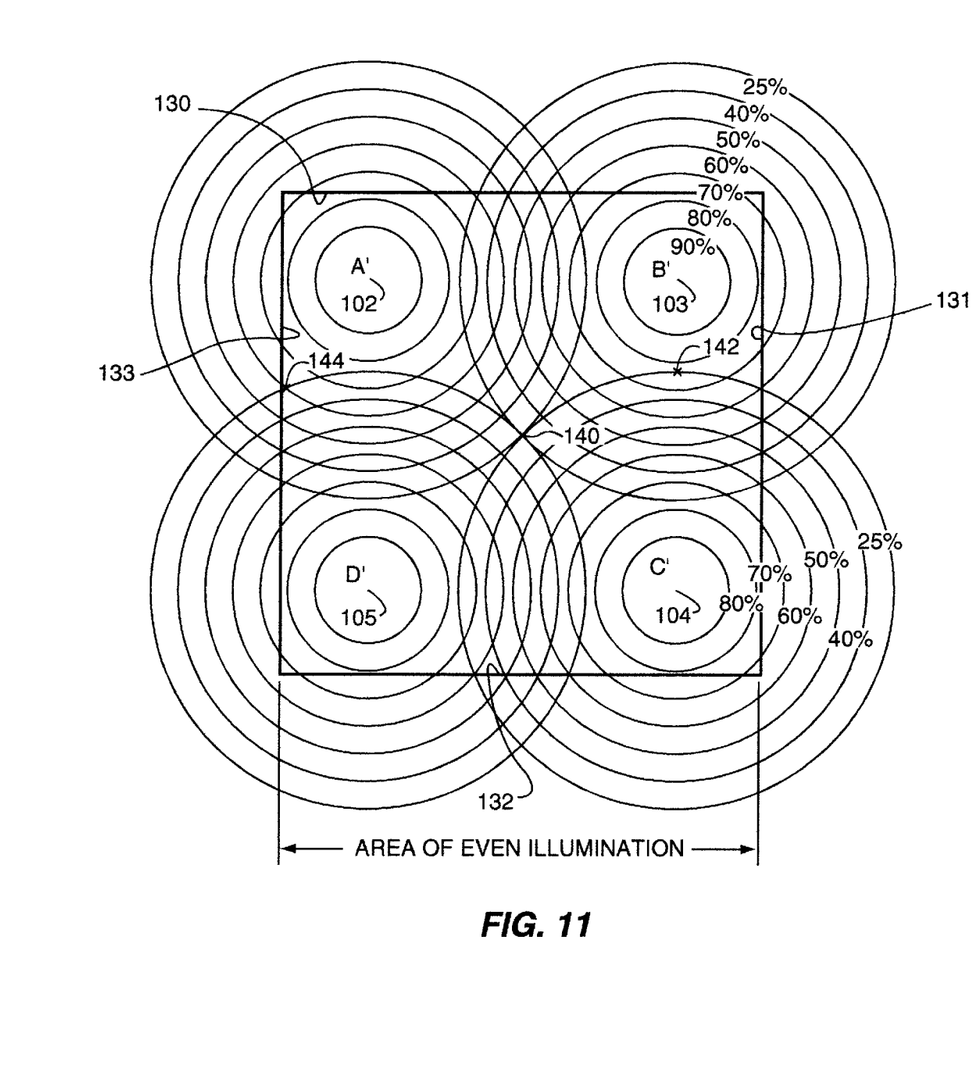
FIG. 11 is a plot of overlapping illumination patterns from a plurality of LEDs arranged in the predetermined manner.

FIG. 11 illustrates a plot of optical power for an LED light source having the LEDs arranged into four quadrants A–D 96–99 as shown in FIG. 8. Referring to FIGS. 8 and 11, each LED located in quadrant A 96 is pointed such that its light distribution is centered in quadrant A' 102, while each LED located in quadrant B 97 is positioned such that its light pattern is centered in quadrant B' 103. The LEDs located in quadrants C and D are arranged such that their patterns are centered in quadrants C' 104 and D' 105, respectively. The center of each of the quadrants A'–D' 102–105 is selected such that the light distribution in a certain area on the bottom surface 94 will be between 80%–100% of peak optical output (this provides distribution within the area of ±10%). For example, boundary lines 130–133 represent the boundary of a region on the bottom surface 94 (FIG. 8) within which the intensity of the light will be between 80%–100% of the peak optical power, when each of the LEDs in a quadrant (e.g., quadrant A 96) is pointed to illuminate its corresponding area (e.g., A' 102) on the bottom surface 94.

Consider for example a first location 140, which represents a spot where the light output is 100% of the peak optical power since the LEDs in quadrants A'–D' 102–105 each contribute 25% of their optical peak power. Similarly, a second location 142 represents a location where the optical power is approximately 100%, since the LEDs which are positioned to illuminate quadrant B' 103 contributes a light output of about 75% of peak optical power at location 142, while the LEDs positioned to illuminate quadrant C' 104 contribute approximately 25% peak optical power at location 142. At a third location 144, the LEDs from quadrants A' 102 and D' 105 contribute about 60% and 25% optical peak power, respectively, while the remaining 5% (concentric circle not shown) comes from the LEDs in quadrants B' 103 and C' 104.

Since the light within the region bounded by lines 130–133 is relatively uniform, a lambertain diffuser is no longer required to generate a uniform light field suitable for machine vision systems. Instead, a more efficient diffuser 52 (FIGS. 3 and 6B) can be employed to enhance the uniformity of the already relatively uniform light field. In one embodiment, the diffuser 52 is an injected molded, optically transparent, plastic component which operates to break up the light from the LEDs impinging on the diffuser.

A preferred diffuser is an injection molded part which has a surface grain pattern which breaks up the light passing through the diffuser to provide a more uniform light output which illuminates the object under inspection. It has been found that an alloy such as stainless steel when etched in a mixture of sulfuric and hydroflouric acids yields a useful grain pattern. The stainless steel is first polished, and then immersed in the sulfuric and hydroflouric acids to reveal the grain boundaries. The shape, size and sharpness of the grain pattern are characteristics of the alloy used, and heat treatment of the alloy during its manufacturing. The depth of each grain pattern is related to the time interval of immersion. By iterative etch steps, an alloy plate is obtained having a pattern which can be used as a die for injection molding. It has been found that forming an injection molded diffuser from a die constructed in this manner produces a diffuser having a non-planar surface 53 which has the property of providing the amount of diffusion necessary to eliminate "hot" spots from each LED without changing the general direction of the light. The diffuser is also relatively inexpensive, and a repeatable part to make during manufacturing.

It is contemplated that a lenslet may also provide an efficient diffuser suitable for use within the light source of the present invention. A lenslet includes a plurality of impressions on an optically transparent surface which tend to focus incident light into a cone of an apex angle depending on the focal length of the lenslets. The efficiency of these diffusers is generally very high since the characteristics of the impression on the lenslet substrate can be controlled and closely matched during manufacturing.

Along with pointing the LEDs during manufacturing such that they point in a predetermined manner to more efficiently take advantage of the light generated by the light source (i.e., the light which actually illuminates the object), the LEDs can also be presorted/screened during manufacturing to categorize each LED based upon the amount of light it generates. During the screening each LED is individually powered and the light emitted from the LED is input to a light meter (e.g., formed by an integrating sphere, a silicon cell and amplifier and a voltage meter) to obtain a measure of the amount of light generated by the LED. The LEDs can then be placed into one of a plurality of illumination categories. When the light source is being assembled, a number of LEDs from each category should be selected and placed into the base plate based upon the relative power ranking. Selecting the LEDs in this manner ensures that each quadrant (e.g., A' 102) is illuminated with the same optical power as adjacent quadrants (e.g., B' 103).

Although the LEDs of the light source of the present invention may be arranged to illuminate four overlapping quadrants as shown in FIG. 10, the present invention is clearly not so limited. All the LEDs in the light source may be aimed at a single quadrant, or at a plurality of quadrants. In addition, the quadrants can be arranged along a single dimension rather than along two dimensions as shown in FIG. 2. The LEDs can also be screened and categorized during manufacturing and based upon angular beam spread of the light (i.e., quantity $\alpha_1+\alpha_2$) to ensure that only LEDs with relatively equal beam spreads are used in the light source.

In addition, although in a preferred embodiment the LEDs generate red visible light, one of ordinary skill will appreciate that the present invention is clearly not so limited, and that any type of LED, including those which generate infrared light may be used depending upon the application of the inspection system.

Although the present invention has been shown and described with respect to several preferred embodiments thereof, various changes, omissions and additions to the form and detail thereof, may be made therein, without departing from the spirit and scope of the invention.

What is claimed is:

1. A method for constructing a machine vision lighting system having a plurality of light emitting diodes, each mounted in a respective mounting hole in a baseplate, for illuminating a predetermined area comprising the steps of:

locating each of the light emitting diodes in the respective mounting hole so that a light-emitting end extends from a first face of the base plate and a lead wire end extends from a second opposing face of the baseplate, including defining each respective mounting hole with a clearance from a surface of the light emitting diode wherein the light emitting diode is movable in the respective mounting hole in three dimensions within a predetermined range of movement;

applying an uncured adhesive between each of the light emitting diodes and a hole edge that defines the respective mounting hole, including applying adhesive over the lead wire end of each of the light emitting diodes when each of the light emitting diodes is located in the respective mounting hole so that the adhesive extends beyond a perimeter of the lead wire end into contact with the adhesive on the hole edge;

providing an alignment fixture having a location for mounting the baseplate and a target surface positioned remote from the mounting surface and in optical communication the light emitting end of each of the light emitting diodes;

defining on the target surface a plurality of illumination sectors;

selectively illuminating each of the light emitting diodes, in turn, and, while each of the light emitting diodes is illuminated, moving an illuminated one of the light emitting diodes within the respective mounting hole so that light from the illuminated one is focused substantially in a predetermined sector of the plurality of sectors according to a predetermined lighting pattern;

separately curing the adhesive applied to each of the light emitting diodes after each of the light emitting diodes is moved according to the moving step to, thereby, permanently secure each of the diodes;

removing the baseplate from the mounting surface; and locating a non-Lambertian light transmission surface over the plurality of light emitting diodes.

2. The method as set forth in claim 1 wherein the step of curing includes selectively curing the adhesive of each of the light emitting diodes in turn after each of the diodes is moved by the moving step and before another of the diodes is moved by the moving step.

3. The method as set forth in claim 1 wherein the step of applying comprises applying a liquid light-curable adhesive.

4. The method as set forth in claim 3 wherein the step of curing comprises exposing each of the light emitting diodes to a UV radiation source.

* * * * *